United States Patent [19]

Kennedy et al.

[11] Patent Number: 4,831,156
[45] Date of Patent: May 16, 1989

[54] 3-SUBSTITUTED 2-ALKYL INDOLE DERIVATIVES

[75] Inventors: Thomas P. Kennedy, Memphis; George W. Kabalka, Knoxville, both of Tenn.

[73] Assignee: The University of Tennessee Research Corp., Knoxville, Tenn.

[21] Appl. No.: 103,487

[22] Filed: Sep. 30, 1987

[51] Int. Cl.$^4$ .................. C07D 209/12; C07D 209/04
[52] U.S. Cl. ................................... 548/494; 548/511; 548/509
[58] Field of Search ............... 548/506, 511, 509, 494

[56] References Cited

U.S. PATENT DOCUMENTS

| | | | |
|---|---|---|---|
| 3,248,401 | 4/1966 | Tondeur et al. | 549/400 |
| 3,627,763 | 12/1971 | Jaeggi et al. | 549/400 |
| 3,810,991 | 5/1974 | Binon et al. | 549/400 |
| 3,818,035 | 6/1974 | Binon | 549/400 |
| 3,891,648 | 6/1975 | Descamps et al. | 549/400 |
| 3,917,600 | 11/1975 | Descamps et al. | 549/400 |
| 3,920,707 | 11/1975 | Descamps et al. | 549/400 |
| 3,929,836 | 12/1975 | Fothergill et al. | 549/400 |
| 3,931,240 | 1/1976 | Binon et al. | 549/400 |
| 3,972,900 | 8/1976 | Fothergill et al. | 549/400 |
| 4,007,204 | 2/1977 | Descamps et al. | 549/400 |
| 4,485,112 | 11/1984 | Pestellini et al. | 549/400 |

OTHER PUBLICATIONS

Spectroscopic Studies of Cutaneous Photosensitizing Agents-IX. A Spin Trapping Study of the Photolysis of Amiodarone and Desethylamiodarone. Anson S. W. Li and Colin F. Chingnell *Photochemistry and Photobiology*, vol. 45, No. 2, pp. 191-197, Feb. 1987.
The Effect on Atrial and Ventricular Intracellular Potentials, and Other Pharmacological Actions of L9146, a Non-Halogenated Benzo(b)Thiophene Related to Amiodarone. E. M. Vaughan Williams, L. Salako and H. Whitting., *Cardiovascular Research*, 1977, 11, 187-197.
Title: Medical Intelligence Drug Therapy–Amiodarone. Author: Jay W. Mason. Publication: The New England Journal of Medicine, vol. 316, No. 8, Feb. 19, 1987.

Primary Examiner—Mary C. Lee
Assistant Examiner—Robert C. Whittenbaugh
Attorney, Agent, or Firm—Luedeka, Hodges & Neely

[57] ABSTRACT

The disclosure relates to compounds of the formula

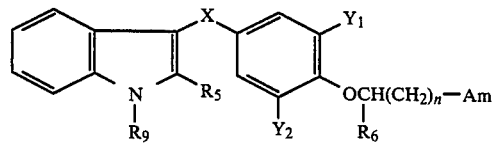

and pharmaceutically acceptable addition salts thereof wherein X represents a substituted or unsubstituted alkylene chain containing 1 to 4 carbon atoms, wherein $R_5$ is a lower alkyl group, wherein $R_6$ is either hydrogen or methyl, $R_9$ is hydrogen or lower alkyl, wherein Am is selected from the class consisting of amino, lower mono and dialkylamino, piperidino, piperazino, N-lower alkyl piperazino, pyrrolidino, and morpholino groups, wherein $Y_1$ and $Y_2$ are identical and are hydrogen, halogen, methyl or ethyl and n is an integer in the range of 1-5.

6 Claims, No Drawings

3-SUBSTITUTED 2-ALKYL INDOLE DERIVATIVES

The U.S. Government has rights in the invention disclosed and claimed in this application pursuant to NIOSH Grant No. R01-0H02264-01.

The invention relates to compounds having pharmacological activity and more particularly relates to novel pharmacologically active 3-substituted 2-alkyl indole derivatives, and methods for their preparation.

Compounds in accordance with the invention are represented by the general formula:

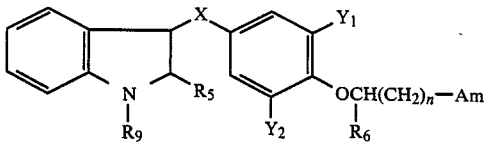 I and pharmaceutically acceptable addition salts thereof wherein X represents a substituted or unsubstituted alkylene chain containing 1 to 4 carbon atoms, wherein $R_5$ is a lower alkyl group, wherein $R_6$ is either hydrogen or methyl, $R_9$ is hydrogen or lower alkyl, wherein Am is a group selected from the class consisting of amino, lower mono and dialkylamino, piperidino, piperazino, N-lower alkyl piperazino, pyrrolidino, and morpholino groups, wherein $Y_1$ and $Y_2$ are identical and are hydrogen, halogen, methyl or ethyl, and n is an integer in the range of 1-5.

The term "unsubstituted or substituted alkylene chain containing 1 to 4 carbon atoms" is intended, unless further defined, to designate a saturated aliphatic hydrocarbon chain of between 1 and 4 carbon atoms with or without one or more substituents. Substituents are limited to those which do not diminish the pharmacological activity of the compounds below a useful level and include branched or straight-chain alkyl or cycloalkyl groups, aryl groups, alkoxy groups, and ester substituents. "Lower alkyl" is intended to designate straight-chain, branched, or cyclic saturated aliphatic hydrocarbon groups containing 1-6 carbon atoms. "Lower mono and dialkylamino" refers to amino groups with one or two straight-chain, branched or cyclic saturated aliphatic hydrocarbon groups containing 1-6 carbon atoms. When two groups are present, they may be the same or different. Examples are methylamino, dimethylamino, ethylamino, diethylamino, n-propylamino, isopropylamine, and the like. Halogen, unless further defined, is intended to refer to fluorine, chlorine, bromine, and iodine.

Compounds in accordance with the invention are useful as vasodilators and as antiarrythmic agents. Preferred for this purpose are compounds of Formula I above wherein X represents the Formula

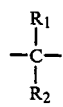

above wherein $R_1$ and/or $R_2$ are hydrogen, lower alkyl groups, groups with the Formula $—OR_3$ with $R_3$ being a lower alkyl group, or groups with the Formula

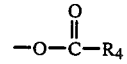

with $R_4$ being hydrogen or a lower alkyl group, $R_5$ is a lower alkyl group containing 1-4 carbon atoms, $R_6$ is hydrogen, $R_8$ is hydrogen or lower alkyl, Am is as defined above for Formula I, $Y_1$ and $Y_2$ are identical and are hydrogen, bromine, iodine, or methyl, and n is in the range of 1-3. Particularly preferred are compounds wherein X is

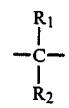

wherein $R_2$ is hydrogen and $R_1$ is hydrogen, or $—OR_3$ with $R_3$ being a lower alkyl group, or $R_1$ is

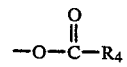

with $R_4$ being hydrogen or a lower alkyl group, $R_5$ is butyl, $R_6$ is hydrogen, $R_9$ is hydrogen, methyl, or ethyl, Am is amino or lower mono and dialkyl amino, $Y_1$ and $Y_2$ are identical and are hydrogen, bromine, iodine, or methyl and n is an integer in the range of 1-3. Most preferably, X is

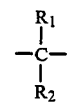

wherein $R_2$ is hydrogen and $R_1$ is hydrogen or $—OR_3$ with $R_3$ being a lower alkyl group containing between 1 and 4 carbon atoms, or $R_1$ is

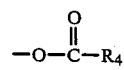

with $R_4$ being hydrogen or a lower alkyl group containing 1 to 4 carbon atoms, $R_5$ is n-butyl, $R_6$ is hydrogen, $R_9$ is hydrogen, methyl, or ethyl, Am is amino, ethylamino or diethylamino, $Y_1$ and $Y_2$ are either both hydrogen, both iodine, or both methyl, and n is 1. Of the most preferred compounds, compounds where $R_1$ and $R_2$ are both hydrogen are particularly desirable.

Compounds of Formula I in which $R_6$ is hydrogen are prepared by first condensing an alkali metal salt of a compound represented by Formula II below in which X, $R_5$, $R_9$, $Y_1$ and $Y_2$ have the same meanings as in Formula I with a dibromoalkane represented by Formula III in which $R_6$ is hydrogen and n is 1-5 in an inert organic medium such as dimethyl formamide. (When $R_9$ is to be hydrogen it is desirable for $R_9$ in Formula II to be a ready-removable protective group such as acetyl.)

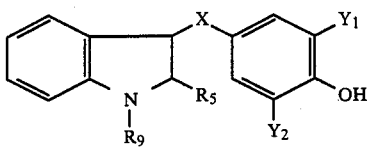
II

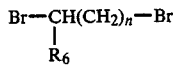
III

The resulting bromoalkoxy-substituted compounds of Formula IV are condensed with an amine of the Formula V in which Am has the same meaning as in Formula I in an inert solvent such as benzene to produce the Formula I compounds.

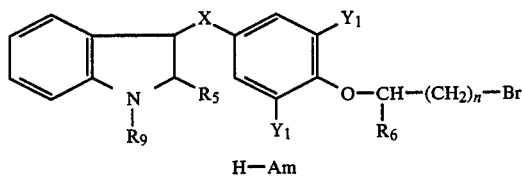
IV

H—Am V

Alternately, when Am does not represent a secondary amine and $R_6$ is either hydrogen or methyl, an alkali metal salt of a compound of Formula II can be condensed with an amine represents by Formula VI in which Z is a halogen atom to produce of Formula I compounds.

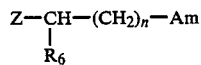
VI

The compounds represented by Formula II can be synthesized by a number of reaction routes. As will become more apparent hereinafter, many of such compounds can be prepared by reduction of or reduction and subsequent reaction of a ketone intermediate represents by Formula VII wherein A is a single direct bond or a substituted or unsubstituted alkaline chain containing 1–3 carbon atoms in the chain and $R_5$, $R_9$ (or protective group), $Y_1$, and $Y_2$ are as defined in Formula I.

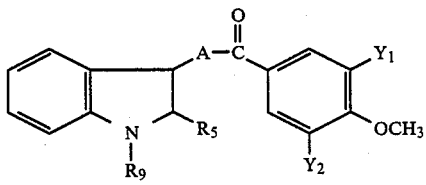
VII

To produce compounds according to Formula II from Formula VII ketones wherein $Y_1$ and $Y_2$ are identical halogens, reduction of the compounds of Formula VII with $Y_1$ and $Y_2$ being halogens is performed under conditions which reduce the ketone group to an alcohol intermediate without otherwise affecting the molecule. A reducing system employing sodium borohydride in a tetrahydrofuran-methanol mixture (10:1 v/v) at approximately 0° C. produces high yields of the alcohol represented by Formula VIII:

VIII

To prepare compounds of the invention wherein $Y_1$ and $Y_2$ are both hydrogen, both methyl, or both ethyl, the ketones of the Formula VII wherein $Y_1$ and $Y_2$ are both hydrogen, both methyl, or both ethyl are similarly reduced to produce the alcohol intermediate shown in Formula IX. Alternately, to produce the compounds where $Y_1$ and $Y_2$ are both hydrogen, reduction of Formula VII compounds wherein $Y_1$ and $Y_2$ are both halogens can be performed employing a reduction system which reduces the ketone group to the alcohol while also dehalogenating the benzene ring to produce Formula IX alcohols. Sodium borohydride in methanol in the presence of a $PdCl_2$ catalyst at 20° C. is a preferred reduction system to achieve both reduction and dehalogenation.

IX

Compounds of Formulas X and XI are produced from the intermediates of Formulas VIII and IX by further reduction at the alcohol group. Compounds of Formula X ($Y_1$ and $Y_2$ are both halogens, methyl or ethyl) or XI ($Y_1$ and $Y_2$ are both hydrogen), when reacted in a suitable solvent at 0° C. with sodium borohydride in trifluoroacetic acid produce compounds at Formulas X and XI, respectively.

X

XI

The alcohols of Formulas VIII and IX can also be employed as intermediates to produce compounds represented by Formulas XII and XIII. A Williamson synthesis whereby the alcohols of Formula VIII or IX are converted to the corresponding alkyoxide and reacted with an alkyl halide of the Formula $R_3X$ is used to produce the ethers represented by Formulas XII ($Y_1$ and $Y_2$ are both halogens, methyl, or ethyl) and XIII ($Y_1$ and $Y_2$ are both hydrogen).

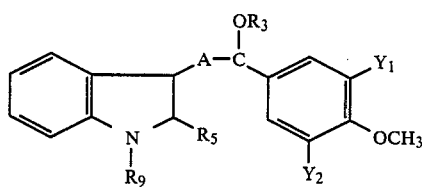 XII

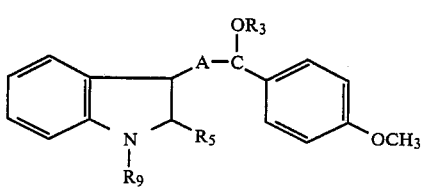 XIII

To produce the compounds of Formulas XIV and XV, the alcohols are esterified. Acyl halides of the Formula

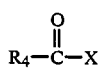

can be reacted with the alcohols of Formulas VIII or IX, respectively, preferably in the presence of a solvent capable of acting as an acid scavenger, e.g., pyridine, to produce compounds of Formulas XIV ($Y_1$ and $Y_2$ are both halogen, methyl, ethyl) or XV ($Y_1$ and $Y_2$ are both hydrogen), respectively:

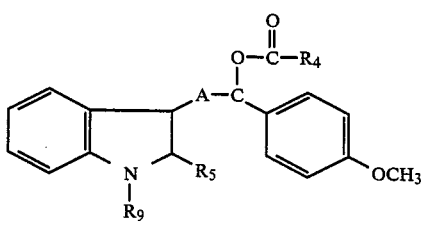 XIV

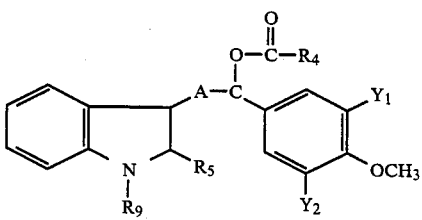 XV

Compounds of the Formulas X–XV can be demethylated with pyridine hydrochloride to yield Formula II compounds.

When A represents a single direct bond or substituted or unsubstituted alkalene chain containing 0–3 carbon atoms, the ketone intermediates represented by Formula VII can be prepared by Friedel-Crafts acylation of a 2,6-substituted anisole of Formula XVII with an acid chloride of Formula XVI wherein m represents an integer of 0–3 and $R_7$ and $R_8$ represent the same entities as $R_1$ and $R_2$ or precursors thereof.

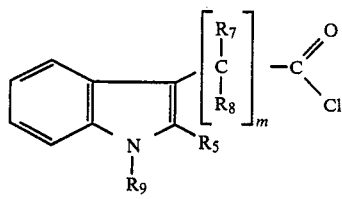 XVI

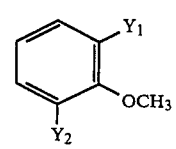 XVII

The acid chlorides of Formula XVI can be prepared from 3-carboxy-2-alkyl indoles of Formula XVIII by reaction in the presence of $CdCl_3$ with an alkene Grignard reagent of Formula XIX wherein o is 0–2 and $R_7$ and $R_8$ are defined as in Formula XVI to result in the formation of the secondary alcohols of Formula XX.

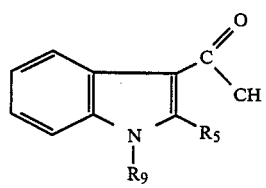 XVIII $$BrMg-\left[\begin{array}{c}R_7\\|\\C\\|\\R_8\end{array}\right]_o-C=CH_2 \quad \text{XIX}$$

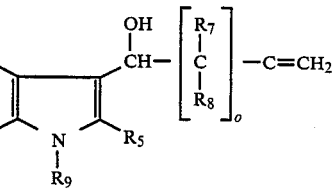 XX

Formula XX alcohols can be dehydrated to the corresponding alkenes of Formula XXI below by reaction with sulfonyl chloride in pyridine followed by reaction with lithium triethyl borohydride. Formula XXI alkene substituted indole compounds are converted to acid chlorides of Formula XVI by ozination in the presence of zinc and oxidation of the resulting aldehyde of Formula XXII to the carboxylic acid employing potassium permanganate (cold) followed by reaction with sulfonyl chloride.

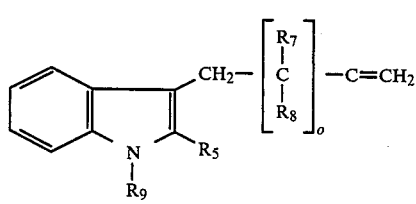 XXI

-continued

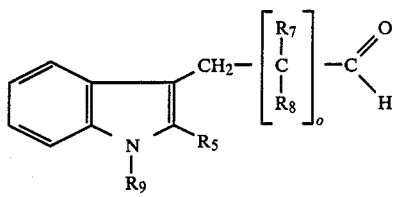

The compounds of Formula I react to form acid addition salts with pharmaceutically acceptable acids, for example, with inorganic acids, such as hydrochloric acid, hydrobromic acid, sulphuric acid and phosphoric acid and with organic acids such as acetic acid, tartaric acid, maleic acid, citric acid and toluenesulfonic acid.

The compounds of the Formula I above and the salts thereof are useful in treating arrhythmic conditions and conditions for which treatment with a vasodialator is indicated. The novel pharmaceutically active agents provided by the present invention can be administered in pharmaceutical dosage forms, internally, for example, parenterally or enterally with dosage adjusted to fit the exigencies of the therapeutic situation. The pharmaceutical dosage forms are prepared by incorporating the active ingredient in conventional liquid or solid vehicles to thereby provide emulsions, suspensions, tablets, capsules, powders and the like according to acceptable pharmaceutical practices. A wide variety of carriers or diluents as well as emulsifying agents, dispersing agents and other pharmaceutically acceptable adjuvants can be incorporated in the pharmaceutical dosage forms.

What is claimed is:

1. A compound of the formula:

or a pharmaceutically acceptable addition salt thereof wherein X represents a branched or straight alkylene chain containing 1 to 4 carbon atoms, wherein $R_5$ is a lower alkyl group, wherein $R_6$ is either hydrogen or methyl, wherein $R_9$ is a hydrogen or lower alkyl, wherein Am is a group selected from the group consisting of amino and lower mono and dialkylamino groups, wherein $Y_1$ and $Y_2$ are identical and are selected from the group consisting of hydrogen, halogen, methyl and ethyl and n is an integer in the range of 1–5.

2. A compound of the formula

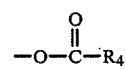

or a pharmaceutically acceptable addition salt thereof wherein X represents an alkylene chain having the formula

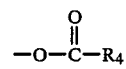

wherein $R_1$ and $R_2$ are each selected from the group consisting of hydrogen, a group having the formula —$OR_3$ with $R_3$ being a lower alkyl group, and a group having the formula $$-O-\overset{O}{\underset{\|}{C}}-R_4$$

with $R_4$ being hydrogen or a lower alkyl group, $R_5$ is hydrogen, $R_9$ is hydrogen or lower alkyl, Am is selected from the group consisting of amino and lower mono and dialkylamino and $Y_1$ and $Y_2$ are identical and are selected from the group consisting of hydrogen, bromine, iodine, and methyl and n is an integer in the range of 1–3 and $R_6$ is hydrogen or methyl.

3. A compound as set forth in claim 2 wherein $R_2$ is hydrogen and $R_1$ is selected from the group consisting of hydrogen, a group having the formula —$OR_3$ with $R_3$ being a lower alkyl group, and a group having the formula $$-O-\overset{O}{\underset{\|}{C}}-R_4$$

with $R_4$ being hydrogen or a lower alkyl group, $R_5$ is butyl, $R_6$ is hydrogen, $R_9$ is hydrogen, methyl, or ethyl, Am is selected from the group consisting of amino, ethylamino, and dialkylamino, $Y_1$ and $Y_2$ are identical and are selected from the group consisting of hydrogen, iodine, and methyl and n is an integer in the range of 1–3.

4. A compound as set forth in claim 2 wherein $R_2$ is hydrogen and $R_1$ is selected from the group consisting of hydrogen, —$OR_3$ with $R_3$ being a lower alkyl group containing between 1 and 4 carbon atoms,

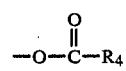

with $R_4$ being hydrogen or a lower alkyl containing 1–4 carbon atoms, $R_5$ is n-butyl, $R_6$ is hydrogen, $R_9$ is hydrogen, methyl, or ethyl, Am is amino, ethylamino or diethylamino, $Y_1$ and $Y_2$ are identical and are selected from the group consisting of hydrogen, iodine, and methyl, and n is 1.

5. A compound as set forth in claim 4 wherein both $R_1$ and $R_2$ are hydrogen.

6. A compound as set forth in claim 2, wherein $R_4$ is butyl.

* * * * *

UNITED STATES PATENT AND TRADEMARK OFFICE
CERTIFICATE OF CORRECTION

PATENT NO. : 4,831,156                        Page 1 of 2

DATED : May 16, 1989

INVENTOR(S) : Thomas P. Kennedy and George W. Kabalka

It is certified that error appears in the above-identified patent and that said Letters Patent is hereby corrected as shown below:

Column 1, line 53, "isopropylamine" should be -- isopropylamino --.

Column 2, line 9, "$R_8$" should be -- $R_9$ --.

Column 3, line 31, "represents" should be -- represented --.

Column 3, line 45, "represents" should be -- represented --.

Column 3, line 46, "alkaline" should be -- alkalene --.

Column 5, line 32, after "methyl" insert -- or --.

UNITED STATES PATENT AND TRADEMARK OFFICE
CERTIFICATE OF CORRECTION

PATENT NO. : 4,831,156

DATED : May 16, 1989

INVENTOR(S) : Thomas P. Kennedy and George W. Kabalka

It is certified that error appears in the above-identified patent and that said Letters Patent is hereby corrected as shown below:

Column 6, line 20, "$CdCl_3$" should be -- $CdCl_2$ --

Formula XVIII

   should be

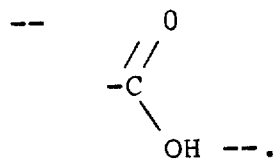.

Signed and Sealed this

Thirteenth Day of March, 1990

Attest:

JEFFREY M. SAMUELS

Attesting Officer       Acting Commissioner of Patents and Trademarks